United States Patent
Khouri

(10) Patent No.: US 9,974,644 B2
(45) Date of Patent: *May 22, 2018

(54) METHOD AND SYSTEM FOR PREPARING SOFT TISSUE FOR GRAFTING, ENHANCING GRAFTING RESULTS, AND GRAFTING AUTOLOGOUS FAT AND ADIPOCYTE DERIVED STEM CELLS TO SOFT TISSUE SUCH AS THE BREAST AND OTHER TISSUE DEFECTS

(71) Applicant: Roger Khouri, Key Biscayne, FL (US)

(72) Inventor: Roger Khouri, Key Biscayne, FL (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 14/707,591

(22) Filed: May 8, 2015

(65) Prior Publication Data
US 2016/0051333 A1 Feb. 25, 2016

Related U.S. Application Data

(63) Continuation of application No. 12/298,011, filed as application No. PCT/US2007/067202 on Apr. 23, 2007, now Pat. No. 9,028,526, which is a continuation of application No. 11/409,294, filed on Apr. 21, 2006, now Pat. No. 8,066,691.

(51) Int. Cl.
| A61F 2/12 | (2006.01) |
| A61B 17/00 | (2006.01) |
| A61B 17/30 | (2006.01) |
| A61B 90/17 | (2016.01) |
| A61B 90/00 | (2016.01) |

(52) U.S. Cl.
CPC ............... *A61F 2/12* (2013.01); *A61B 90/02* (2016.02); *A61B 90/17* (2016.02); *A61B 2017/00792* (2013.01); *A61B 2017/00796* (2013.01); *A61B 2017/00969* (2013.01); *A61B 2017/308* (2013.01); *A61B 2217/005* (2013.01); *A61B 2562/0247* (2013.01); *A61F 2210/0004* (2013.01)

(58) Field of Classification Search
CPC .... A61F 2/12; A61F 2210/0004; A61B 90/02; A61B 90/17; A61B 2562/0247; A61B 2217/005; A61B 2017/00796; A61B 2017/308; A61B 2017/00969; A61B 2017/00792

See application file for complete search history.

(56) References Cited

U.S. PATENT DOCUMENTS

| 4,574,780 | A | 3/1986 | Manders |
| 5,098,331 | A | 3/1992 | Corrado |
| 5,536,233 | A | 7/1996 | Khouri |
| 5,662,583 | A | 9/1997 | Khouri |
| 5,676,634 | A | 10/1997 | Khouri |
| 5,695,445 | A | 12/1997 | Khouri |
| 5,701,917 | A | 12/1997 | Khouri |
| 6,238,908 | B1 | 5/2001 | Armstrong et al. |
| 6,478,656 | B1 | 11/2002 | Khouri |
| 6,500,112 | B1 | 12/2002 | Khouri |
| 6,641,527 | B2 | 11/2003 | Khouri |
| 6,699,176 | B1 | 3/2004 | Khouri |
| 2002/0198474 | A1 | 12/2002 | Becker |
| 2003/0105469 | A1 | 6/2003 | Karmon |
| 2005/0025755 | A1 | 2/2005 | Hedrick et al. |
| 2005/0245850 | A1 | 11/2005 | Freyre et al. |
| 2009/0312746 | A1 | 12/2009 | Khouri |

FOREIGN PATENT DOCUMENTS

| DE | 19711923 | 11/1997 |
| EP | 0421368 | 4/1991 |
| JP | 05239702 | 9/1993 |
| WO | WO-1995-025038 | 9/1995 |

OTHER PUBLICATIONS

Bernard et al., "Autologous Fat Graft in Nipple Reconstruction", *Plastic and Reconstructive Surgery*, vol. 112, No. 4, 964-968, 2003 (5 pages).

(Continued)

*Primary Examiner* — Taeyoon Kim
(74) *Attorney, Agent, or Firm* — Finnegan, Henderson, Farabow, Garrett & Dunner LLP

(57) ABSTRACT

A method is disclosed for preparing a soft tissue site, and augmenting the soft tissue site, such as the breast(s), scar, depression, or other defect, of a subject through use of devices that exert a distractive force on the breast(s) and grafting of autologous fat tissue such as domes with sealing rims for surrounding each of the soft tissue site and a regulated pump. The method for preparing the soft tissue site, and enhancing fat graft results, entails application of the distracting force to the targeted soft tissue site at least intermittently for some period of time and preferably several weeks prior to the graft procedure. A related aspect of the invention includes following the preparation steps by transfer of fat from other areas of the subject to the subject's soft tissue site, and then reapplication of the distractive force to the soft tissue site that received the autologous fat graft. Alternatively, fat from genetically related sources may be used, and the fat may be further processed prior to injection. Substantial soft tissue augmentation, high rates of graft survival and negligible graft necrosis (data demonstrating 80% survival and only 20% necrosis is presented) or calcification result from the practice of these methods.

34 Claims, 7 Drawing Sheets

(56) References Cited

OTHER PUBLICATIONS

Brandow et al., "Facial Multilayered Micro Lipo-Augmentation", *International Journal of Aesthetic and Restorative Surgery*, vol. 4, No. 2, 95-110, 1995 (16 pages).
Coleman et al., "Fat Grafting to the Breast Revisited: Safety and Efficacy", *Plastic and Reconstructive Surgery*, vol. 119, No. 3, 775-785, 2007 (10 pages).
Cortese et al., "Free Fat Transplantation for Facial Tissue Augmentation", *Journal of Oral and Maxillofacial Surgery*, vol. 58, No. 2, 164-169, 2000 (6 pages).
Fulton, "Breast Contouring with 'Gelled' Autologous Fat: A 10-Year Update", *International Journal of Cosmetic Surgery and Aesthetic Dermatology*, vol. 5, No. 2, 155-163, 2003 (9 pages).
Khouri et al., "Breast Reconstruction and Augmentation Using Pre-Expansion and Autologous Fat Transplantation", *Clinics in Plastic Surgery*, vol. 36, No. 2, 269-280, 2009 (12 pages).
Kiyokawa et al., "Combination Treatment with the Tissue Expander and Dermal Fat Grafting for Sclerodermie en Coup de Sabre", *Japanese Journal of Plastic and Reconstructive Surgery*, vol. 40, No. 10, 1029-1034, 1997 (6 pages).
Markey et al., "Autologous Fat Grafting: Comparison of Techniques", *Dermatologic Surgery: Official Publication for the American Society for Dermatologic Surgery*, vol. 26, No. 12, 1135-1139, 2000 (5 pages).
Rohrich et al., "Liquid Injectable Silicone: Is There a Role as a Cosmetic Soft-Tissue Filler?", *Plastic end Reconstructive Surgery*, vol. 113, No. 4, 1239-1241, 2004 (3 pages).
Shenaq et al., "New Research in Breast Reconstruction: Adipose Tissue Engineering", *Clinics in Plastic Surgery*, vol. 29, No. 1, 111-125, 2002 (15 pages).
Shiffman, "Mammograms in cosmetic breast surgery", *Indian Journal of Plastic Surgery*, vol. 38, No. 2, 100-104, 2005 (5 pages).
Smith, Dr. Joe, *Liposuction 101: Liposuction Textbook*, "Chapter 23: Tumescent Formulations", St. Louis: Mosby, Inc. © 2013, Web, Accessed May 19, 2014 from http://www.liposuction101.com/liposuction-textbook/chapter-23-tumescent-formulations/ (9 pages).
"Stent", *Medline Plus Medical Dictionary from Merriam-Webster*, 2012, from http://www.merriam-webster.com/medlineplus/stent (2 pages).
Yoshimura et al., Characterization of Freshly Isolated and Cultured Cells Derived from the Fatty and Fluid Portions of Liposuction Aspirates, *Journal of Cellular Physiology*, vol. 208, 64-76, 2006 (13 pages).

Evenly disperse grafts..........
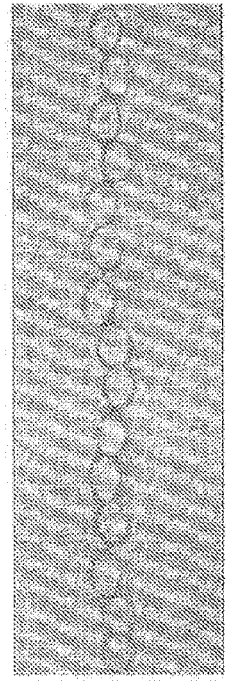
Micro grafts.........
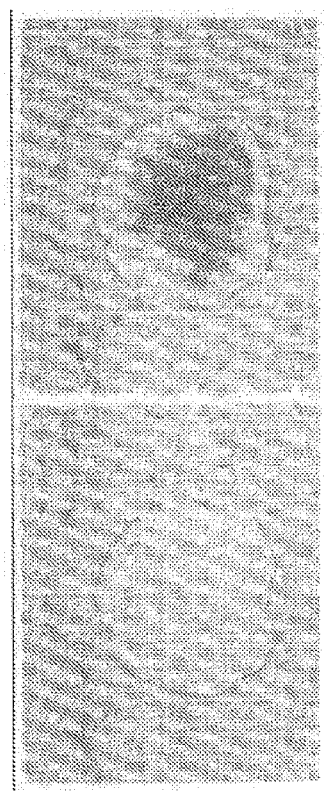
Optimize graft/receipt interface...........
Droplet/Cel at a time..........
Large blobs die..........
Fig. 7

METHOD AND SYSTEM FOR PREPARING SOFT TISSUE FOR GRAFTING, ENHANCING GRAFTING RESULTS, AND GRAFTING AUTOLOGOUS FAT AND ADIPOCYTE DERIVED STEM CELLS TO SOFT TISSUE SUCH AS THE BREAST AND OTHER TISSUE DEFECTS

BACKGROUND OF THE INVENTION

1. Field of the Invention

This invention relates generally to methods of preparing soft tissue, such as breasts, for augmentation and, relatedly, to methods of enhancing fat and adipocyte derived stem cells grafting results, and augmenting and restoring soft tissue by autologous fat and adipocyte derived stem cell grafting.

2. Related Art

There are numerous instances where persons desire augmentation of soft tissue such as their breasts. Other examples of soft tissue augmentation opportunities include the face, the buttocks, depressed scar contours, tissue atrophy related to aging, scarring, radiation or disease, or any body deformity or area that is desirably augmented. Another such instance is for the augmentation or the restoration of one or both breasts subjected to a partial or total mastectomy, a biopsy, or other disfiguring events in order to restore physiological symmetry and psychological well-being. Yet other instances are for correction of natural abnormalities such as scarring and dimpling. Still other instances are for augmentation of the breasts to improve cosmetics and self-esteem.

Liposuctioned fat is known to be rich in stem cells that have the ability to restore and reconstruct various soft tissue defects in response to local differentiation clues from the recipient site. This invention also relates to providing for improved survival of larger graft volumes in a given recipient site.

Prosthetic implants have been developed for insertion below the skin. However, the severity of the potential complications including scarring, implant rupture, capsular contracture, necrosis and implant migration as well as the recent adverse publicity thereof have significantly reduced the desirability of these implants. While scientific evidence is not conclusive, there is some indication that breast implants might contribute to secondary diseases. Thus, there is a societal need for other means to obtain breast augmentation.

Breast augmentation by use of fat grafts was experimentally explored in the past but has not gained widespread acceptance. First, the larger blocks of grafts used then displayed poor survival. Secondly, the failed grafts sometimes produce stellate irregular nodules with calcifications. These nodules, which were often palpable, were occasionally indistinguishable from cancer with the breast imaging technology available at that time. For these reasons certain medical societies and associations advocated a ban on fat grafting to the breast. Consequently, the practice of fat grafting to the breast was contraindicated and not pursued.

Subsequently, digital mammography, high-resolution ultrasound, Magnetic Resonance Imaging (MRI) and its associated absorption curve and fat suppression views have revolutionized breast imaging. As a result, radiologists now have the imaging technology that enables them to differentiate with reasonable certainty a neoplastic process from the fat necrosis commonly left behind following reduction mammoplasties, the now accepted SAL (Suction Assisted Lipectomy) breast reduction methods, breast biopsies, and even non-surgery related every day breast trauma. It is consequently evident that concerns associated with distinguishing areas of fat necrosis resulting from fat grafting to the breast from areas of neoplasia have now been essentially obviated by advances in imaging technology. With these advances, fat grafting may now again be considered for this application.

Described herein is a new method of preparing soft tissue for augmentation, including preferably the breasts, for enhancing fat grafting results in soft tissue, and augmenting soft tissue by use of autologous fat grafts. This may preferably be as general method for preparing a soft tissue recipient to successfully accept the survival of larger graft volumes, whether these are fat droplets, stem cells or other dispersed live cell injections. This method does not suffer from the defects of the previously attempted methods of fat grafting to the breast in that it results in high rates of larger volume graft survival and marked reductions of graft necrosis and calcification. This method is distinguished from previously disclosed methods by, inter alia, the use of devices that exert a distractive force on the breast to increase the volume of the recipient space, increase its vascularity and generate a fertile extracellular fluid matrix which prepares the soft tissue site for improved graft survival. This technique enhances the results in conjunction with improved techniques of autologous fat harvesting, processing and grafting and other techniques of tissue culture.

Soft tissue grafting, augmentation and restoration of tissue loss by dispersion of small micro-grafts is three dimensional grafting which requires novel concepts. Just as in two dimensional grafting, one cannot apply more grafts than the surface area of the defect, and stacking more grafts is counterproductive. In 3D grafting, even with the best and most even dispersion of the finest graft droplets, one cannot graft more than the volume of the recipient site defect (see drawing figure). It follows therefore that expansion, even temporarily, of the recipient space by external distraction would increase its volume and create room for more grafts to survive. In addition, it is well known that tissue expansion is angiogenic, (increases the vascularity) and that improved vascularity leads to more successful engraftment. Furthermore, the increased extracellular fluid matrix of the expanded tissue is rich in growth factors and other agents known to render the site more fertile for graft survival.

SUMMARY OF THE INVENTION

In addition to the foregoing, the invention relates to a method of augmenting soft tissue of the type mentioned herein, including preferably at least one breast of a subject, comprising the steps of applying a distractive force to at least one breast of a subject, removing a sample of fat from another body area of the subject, injecting at least a portion of said sample of fat taken from the subject into said breast that was subjected to a distractive force and then possibly maintaining the distractive force to the breast injected with the subject's fat to immobilize the recipient tissue and help with the engraftment. Use of this method results in substantial augmentation of the subject's breast or breasts while also serving to remove fat from undesirable locations of the body such as the abdomen, thighs, flanks, buttocks (gluteal regions), and trochanters. Use of an autologous graft also reduces the likelihood of graft rejection. The subject may be a human or more particularly a female human.

The invention further relates to preparing a soft tissue site, including preferably the breasts, for augmentation or regeneration of tissue loss to make it more receptive to successful engraftment of liposuctioned fat, adipocyte derived stem cells, or other dispersed tissue graft droplets, through pre-grafting expansion of the soft tissue site.

In practicing a preferred embodiment of the method of this invention, a distractive force is applied to the breast both before and possibly after grafting of fat to the breast. The distractive force may be applied via any number of different methods or devices, both externally and internally. A preferred method for applying a distractive force comprises the application of vacuum pressure to the breast of said subject by use of a device comprising a dome which fits over the fat-receiving breast(s) of the subject, a rim that seals said dome(s) around said breast(s), and a pump for creating a vacuum within the dome(S) around said breast. An external breast tissue expander (the Brava® Breast Enhancement and Shaping System, Brava, LLC; Coconut Grove, Fla.) represents one commercially available and preferred device for applying vacuum pressure to the breast of the subject. Vacuum pressure may be applied to the breast or breasts by a hand pump that may be detachable or by a self-contained vacuum pump system that is connected to the device. This self contained vacuum pump system may comprise an independent power source, a pressure sensor, and a servo-mechanism to maintain a constant vacuum pressure inside said dome. Under certain circumstances, equivalent vacuum pressure may be applied to both breasts in the practice of the invention. However, other circumstances may dictate that different vacuum pressures are applied to each breast, or to only the fat-receiving breast.

The fat sample used in the breast graft is preferably typically removed from at least one of an abdominal region, a thigh region, a flank region, a gluteal region, or a trochanter of said subject. However, the sample of fat may be taken from any suitable region of the subject. Removal of fat is desirably effected by methods that minimize trauma and minimize manipulation or the fat removed from the subject. One suitable method of obtaining the sample of fat is by aspirating the fat from the subject with a syringe. This syringe may be a 10, 20 or 60 ml syringe fitted with a 12 or 14 gauge cannula (i.e. approximately 2-3 min in diameter). The harvested fat is then separated from any fluid such as serum or tumescent fluid that is associated with the fat. These fat removal and separation methods are well known in the medical art.

In an alternative embodiment, the aspirated tissue is processed to concentrate, multiply or increase the number of stem cells present using techniques that are familiar to those of ordinary skill in the art.

The fat or the stem cell sample is preferably then injected into the breast that was previously subjected to a distractive force such as by vacuum pressure. Injection into the breast may preferably be accomplished with a syringe. The syringe may be a 3, 5 or 10 ml syringe fitted with a 12 or 14 gauge cannula (i.e. approximately 2-3 mm in diameter). The injection may be into either one or both of a deep retroglandular space and/or a subcutaneous plane of the breast. The injections are preferably made in a three dimensional fanning pattern to micro-weave the sample of fat in the breast. However, these injections are preferably not made into the breast parenchymal region or a breast glandular region. The preferred method of injecting the fat or dispersed tissue micro-droplet sample is to distribute them throughout the deep retroglandular space and/or the subcutaneous plane of the breast while avoiding the breast parenchyma or breast gland region.

Following injection, a splint like device or bandage is preferably applied to the breast to immobilize the injected fat and facilitate the engraftment process. Alternatively, a distractive force such as vacuum pressure is again applied to the breast. The distractive force such as vacuum pressure may be first applied to the injected breast preferably about 12 to 18 hours after injection of the breast. For the two day period following injection of fat into the breast the vacuum may preferably be intermittently applied to the breast for at least about 6 to 22 hours per day (i.e. 24 hour period) or for as long as possible. After this 2 day (i.e. 48 hour) period, the distractive force such as vacuum pressure may preferably be intermittently applied to the injected breast for at least about 10 hours per day during the entire post injection time period of about 2 to 7 days.

This method may be applied when the subject is as human or, more particularly, a female human. It is further recognized that the entire procedure comprising the steps of applying a distractive force to at least one breast of a subject, removing a sample of fat from the subject with a syringe; injecting at least a portion of said sample of fat taken from the subject into said breast that was subjected to a vacuum with a syringe, and then applying a distractive force to the breast injected with the subject's fat can be repeated on one or more breasts of a subject. Repeating the procedure may be desirable as compared to a single procedure in instances where greater degrees of breast augmentation are sought.

Finally, alternative methods of obtaining dispersed soft tissue cell samples suitable for injection into the subject are further disclosed. Such methods may be important in obtaining some substantial breast augmentation when the subject has limited amounts of fat available for harvesting and injection. These methods might also be important when the tissue grafts have the potential to regenerate lost or scarred tissue not only in the breast but in other organs and parts of the body. In one embodiment, the fat sample may be obtained by removing fat from the subject; processing the tissue to extract the preferred cellular component such as adipocyte derived stem cells, and reinjecting the enriched tissue directly, or further propagating this component outside the subject, and then reinjecting it. In another embodiment, a sample of fat may be obtained by removing a living cell or living cells from the subject, propagating the cell or cells outside of the subject under conditions where the cell or cells will form a sample of fat; and collecting the sample of fat thus formed. Also disclosed are methods of obtaining the sample of fat from sources other than the subject. In one embodiment of the invention, the source of the sample of fat may be obtained from another human, a human that is genetically related to the subject, or a human that is a twin of the subject. Alternatively, the sample of fat may be obtained from a source that is a stem cell or cells derived from a source other than the subject.

The above method of preparing the recipient site with a distractive force applied over a period of time long enough to substantially expand the volume of the recipient tissue prior to grafting can also be applied to graft augmentation of other parts of the body such as depressed scars, wrinkle lines or the subcutaneous fat atrophy that accompanies aging. The method is also a useful way to augment the survival of fat grafting to the buttocks. The method may also be used for the reconstruction of the breast after lumpectomy and radiation and after mastectomy. The method can also be applied to other organs and parts of the body that have been lost to scarring, radiation, disease or aging and that could benefit from an infusion of stem cells or dispersed micrografts of other cell types.

This method pertains to soft tissue three dimensional grafting in general by providing a means of improving the success and engraftment yield of the dispersed soft tissue cells by at least temporary pre-expansion of the recipient site utilizing distractive forces.

Further features and advantages of the present invention, as well as the structure and operation of various embodiments of the present invention, are described in detail below with reference to the accompanying drawings.

BRIEF DESCRIPTION OF THE DRAWINGS

The accompanying drawings, which are incorporated in and form a part of the specification, illustrate the embodiments of the present invention and together with the description, serve to explain the principles of the invention, in the drawings:

FIG. 7 shows a pattern of micrograph tissue graft dispersion n a three dimensional soft tissue block that is even and conducive to successful engraftment. Extrapolating from the known two dimensional state, this three dimensional model illustrates that the limit of graft to recipient volume imposed by crowding and revascularization has to remain below 1, even with the most even dispersion of the smallest micrografts.

DETAILED DESCRIPTION OF THE PREFERRED EMBODIMENTS

Figure 1:
FIG. 1 illustrates the use of an external breast tissue expander (Brava® Breast Enhancement and Shaping System, Brava, LLC; Coconut Grove, Fla.)

In practicing the embodiments of the method of this invention, a preferred method for applying distractive force such as vacuum pressure to the breast of said subject is by use of a device comprising a dome which fits over at least one breast of the subject, a rim that seals said dome around said breast, and a pump for creating a vacuum around said breast. An external breast tissue expander (Brava® Breast Enhancement and Shaping System, Brava, LLC; Coconut Grove, Fla.) represents one preferred device for applying vacuum pressure to the breast of the subject. Descriptions of various devices suitable for applying vacuum pressure to the breast of a subject are described in U.S. Pat. Nos. 6,500,112, 5,676,634, 5,695,445, and 5,536,233 as well as in U.S. patent application Ser. No. 11/101,240, the disclosures of which are incorporated herein by reference in their entirety. However, other devices that exert a distractive force on the breast may also be used in the practice of this invention. For example, U.S. Pat. No. 6,699,176, incorporated herein by reference in its' entirety, discloses other devices that can exert a distractive force on the breast. One such device comprises at least one dome for adhering to a patient s breast, where the dome includes a supporting frame that is inflatable to expand the frame and induce a distractive force in the underlying breast. One skilled in the art would thus understand that the distractive force on the breast may be exerted by either vacuum pressure, by mechanical forces being applied, or by other means in accomplishing certain steps of the method described herein. The distractive force may also be applied internally, through tissue expanders as known in the art which are inserted subcutaneously or with supporting frameworks that are made to gradually expand, etc., all as may be known to those of skill in the art.

Without being limited by theory, and offered only as an observation, the success of the method for breast augmentation by fat grafting disclosed herein may be due to one or more conditions or combinations of conditions induced in the breast by the distractive force created by a vacuum or by other methods. For example, pre-grafting expansion of the breasts by subjecting them to a distractive force before introduction of the fat grab may increase the vascularity of the recipient site and thus result in improved quality of the graft recipient bed thus increasing receptivity and retention (i.e. reduced graft failure). Similarly, pre-treatment of the breast with a distractive force (i.e. pre-grafting expansion of the breast) may provide for more periglandular or interstitial space for greater graft volume injection with less crowding of the injected fat graft droplets. This enlargement of the three dimensional lattice improves the graft to recipient contact interface for better revascularization of the injected fat. Post-graft injection treatment of the breast with an immobilizing device or a distractive force may also hold up the grafts as a stent and promote revascularization or other beneficial processes during the early engraftment period.

In practicing the invention, the distractive three is applied to the breast prior to the initiation of fat grafting. In the examples provided herein, the distractive force is continuously applied for at least 24 hours prior to fat grafting or injection. For about 28 days prior to the period of continuous distractive force application to the breast, an intermittent distractive force is applied to the breast for at least 10 hours per day in the examples. Alternatively, higher distractive throes intermittently applied over shorter periods of time might achieve the same hypervascularity and interstitial space expansion effect. In outlining the time periods of distractive force application used in the examples cited herein, one skilled in the art would clearly understand that minor deviations from these exemplary time periods for application of the distractive force are not expected to significantly impact the results obtained in practicing this invention. It is further contemplated that practitioners may adapt these time periods of distractive force application based on a variety of circumstances pertaining to each particular subject.

The amount of distractive force that is applied to the breast both before and possibly after injection is desirably regulated. When the distractive force is a vacuum, regulation of the vacuum within the dome is important to prevent contusions caused by rupturing capillaries adjacent the surface of the skin. Medical data suggest that these contusions will not occur if vacuum within the dome is maintained at less than about 20-25 mm Hg, at least on a continuous basis. Thus, the vacuum pump is desirably regulated to control the vacuum within the dome to within this limit presuming a protocol involving extended wearing at continuous pressure is followed. In addition, skin ulceration can occur if excessive contact pressures are applied thereto for any extended time period. Medical data suggest that a contact pressure less than 20 mm Hg may be applied indefinitely without such ulceration. However, contusions may occur due to positive contact pressures upon the skin at continuous pressures above this ulceration limit. Alternatively, higher pressures could be intermittently applied for shorter periods of time over a few weeks to achieve the same hypervascularity and expansion effect. The inventor's invention contemplates use not only of one of the several distractive force application methodologies as recited herein but others as well, subject to such further experimentation as would be well within the scope of the teaching and skill of those of ordinary skill in the art. For example, the inventor contemplates that cycled intermittent higher vacuum pressures could be applied for shorter periods of time to achieve similar if not the same results.

Nonetheless, it is envisioned that vacuum pressures falling outside of the range of 20-25 mm Hg may also be employed in the practice of this invention. As discussed in U.S. patent application Ser. No. 11/101,240, incorporated herein by reference in it's entirety, approximately 20,000 external breast tissue expander (Brava® Breast Enhancement and Shaping System, Brava, LLC; Coconut Grove, Fla.) devices have been sold worldwide as of the end of the year 2004, with approximately 10,000 of these sales being made in the U.S. alone. As part of these sales, the buyers were provided medical advice through medical professionals and data including their "wear" history was collected from approximately 78% of them. The recommended regimen required the user to wear the external breast tissue expander at least ten hours per day for ten consecutive weeks. Pressures exerted within the bra ranged within 15 to 33 mm Hg as the vacuum pump cycled off and on, with an average of approximately 22 mm Hg. Users were also advised that wearing the external breast tissue expander for longer time periods would result in greater increases in breast size. As a result, it is believed that many users chose to wear the device more than the ten hours per day and more than ten weeks. However, the recommended "wear" protocol was for ten hours per day for ten fall weeks. As in any recommended protocol, and especially one extending for a significant time period, adjustments were made upon patient request and upon patient initiated change without advice. For some users, requests were granted to increase the maximum pressure to 35 and even 37 mm Hg. It is thus contemplated that under certain circumstances, certain conditions, or during certain periods of time it may be desirable to increase the amount of distractive force applied beyond the recommended range of 20 to 25 mm Hg in the practice of this invention.

The sample of fat for injection into the breast or breasts may be taken from any suitable region of the subject. Subjects are typically placed under local tumescent anesthesia and sedation for the steps of the procedure involving fat removal and fat injection. For example, the fat samples may be harvested from an abdominal region, a thigh region, a flank region, a gluteal region, or a trochanter of said subject. Fat taken from multiple regions may be injected into a breast or breasts. Removal of fat is achieved by methods that minimize trauma and minimize manipulation of the fat removed from the subject. In this regard, a syringe may be used to remove the fat. Manual removal of the fat with a small syringe fitted with a fine diameter cannula is a preferred method of obtaining the fat sample. One example of a preferred method of obtaining the sample of fat is by aspirating the fat from the subject with a 10 ml syringe fitted with a 14 gauge cannula (i.e. approximately 1-2 mm in diameter). The typically employed suction devices that are used in cosmetic surgery to remove fat (i.e. liposuction) may subject the fat to shear forces or other conditions that are less conducive to successful grafting. However, it is recognized that mechanical devices that remove fat under reduced pressures and/or through fine diameter cannulas may also be used to obtain a fat sample useful in the practice of this invention.

Following removal and prier to injection, the harvested fat is then separated from any fluid such as serum or tumescent fluid that is associated with the fat. Such separation may simply be accomplished by placing the filled collection syringe in an upright position and allowing the fat and fluid to separate into two phases. The fluid phase can then be simply expelled from the bottom of the syringe. Alternative methods of separating fat and fluid such as centrifugation or filtration are also contemplated.

Figure 2:
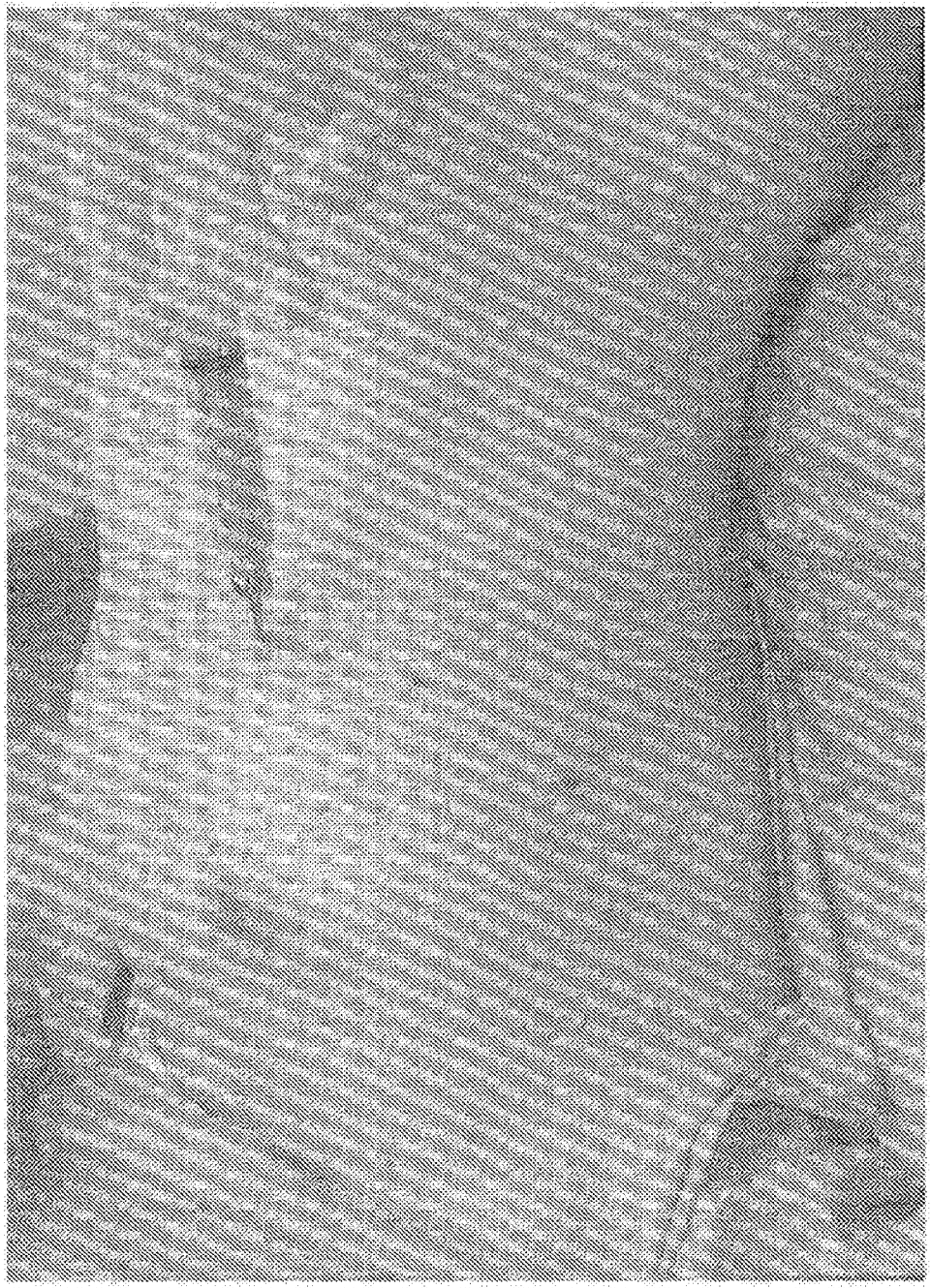
FIG. 2 illustrates the three dimensional fanning pattern of injection used to distribute the autologous fat grafts in a subject.

The fat sample is then injected into the breast that was previously subjected to a distractive force. Injection into the breast may be accomplished with a syringe. The syringe may be a 10 ml syringe, fitted with a 14 gauge cannula (i.e. approximately 1-2 mm in diameter). Injection may be into either one or both of a deep retroglandular space and/or a subcutaneous plane of the breast. The injections are node in a three dimensional fanning pattern to micro-weave the sample of fat in the breast. FIG. 2 illustrates one arrangement of injection ports that can be used to inject the fat sample in a three dimensional fanning pattern. The injection ports are typically placed at regular intervals around both the base of the breast and around the nipple in a circular pattern. A frontal view of the breast post injection would thus show an inner circle of injection in or around the nipple and an outer circle of injection ports around the base of the breast. The cannula that is used to distribute microdroplets or tiny droplets of fat is then inserted at various depths and angles to deliver a diffuse distribution of fat in the desired regions of the breast. A microdroplet is typically between about 25 ul (microliters) to 250 ul in volume. While it is anticipated that tiny droplets are desired, it is only known at present that insertion of large globules of fat need to be avoided. However, injections are preferably not made into a breast parenchyma region or a breast gland region. The preferred method of injecting the fat sample is to use multiple injection ports to distribute microdroplets of the fat sample throughout the deep retroglandular space and/or a subcutaneous plane of the breast while avoiding the breast parenchyma or breast gland region. Avoidance of injection into the breast parenchyma or breast gland region may reduce the incidence graft failure and necrosis. In describing one illustrative pattern of injection ports, it is clearly understood that any other pattern of injection ports that permits a diffuse distribution of the fat graft to the desired regions can be used in the practice of this invention. For example, as grid pattern of injection ports or the use of curved injection cannulas through a more limited number of injection ports (i.e. 1 or 2 sites only) may also be used.

Following injection of the fat into the breasts, a distractive force might be again applied to the breast or breasts. A preferred method for applying distractive force such as vacuum pressure to the breast of said subject is by use of a device comprising a dome which fits over at least one breast of the subject, a rim that seals said dome around said breast, and a pump for creating a vacuum around said breast.

In practicing the invention, the distractive force is possibly applied following the fat grafting or injection. In the examples provided herein, the distractive force is first applied about 12 to 18 hours after completion of fat injection. During the 48 hour period following completion of fat injection, the distractive force is applied to the injected breast as continuously as possible for at least about 6 to 22 hours per day (i.e. 24 hour period) or for as long as possible. After the 48 hour period following completion of fat injection, the distractive force is intermittently applied to the injected breast for at least 10 hours per day for a period of about 2 to 7 days. In outlining the time periods of distractive force application used in the examples cited herein, one skilled in the art would clearly understand that minor deviations from these exemplary time periods for application of the distractive force are not expected to significantly impact the results obtained in practicing this invention. It is further contemplated that practitioners may adapt these time periods of distractive force application based on a variety of circumstances pertaining to each particular subject.

This method may be applied when the subject is a human or, more particularly, a female human. This method may also be employed for other medical or cosmetic needs or desires such as for example in the course of augmenting the breasts of a human undergoing a sexual reversal procedure wherein the breasts of a male human are first augmented by hormonal stimulation and/or surgical alteration to resemble the breasts of a female human.

Figure 9:
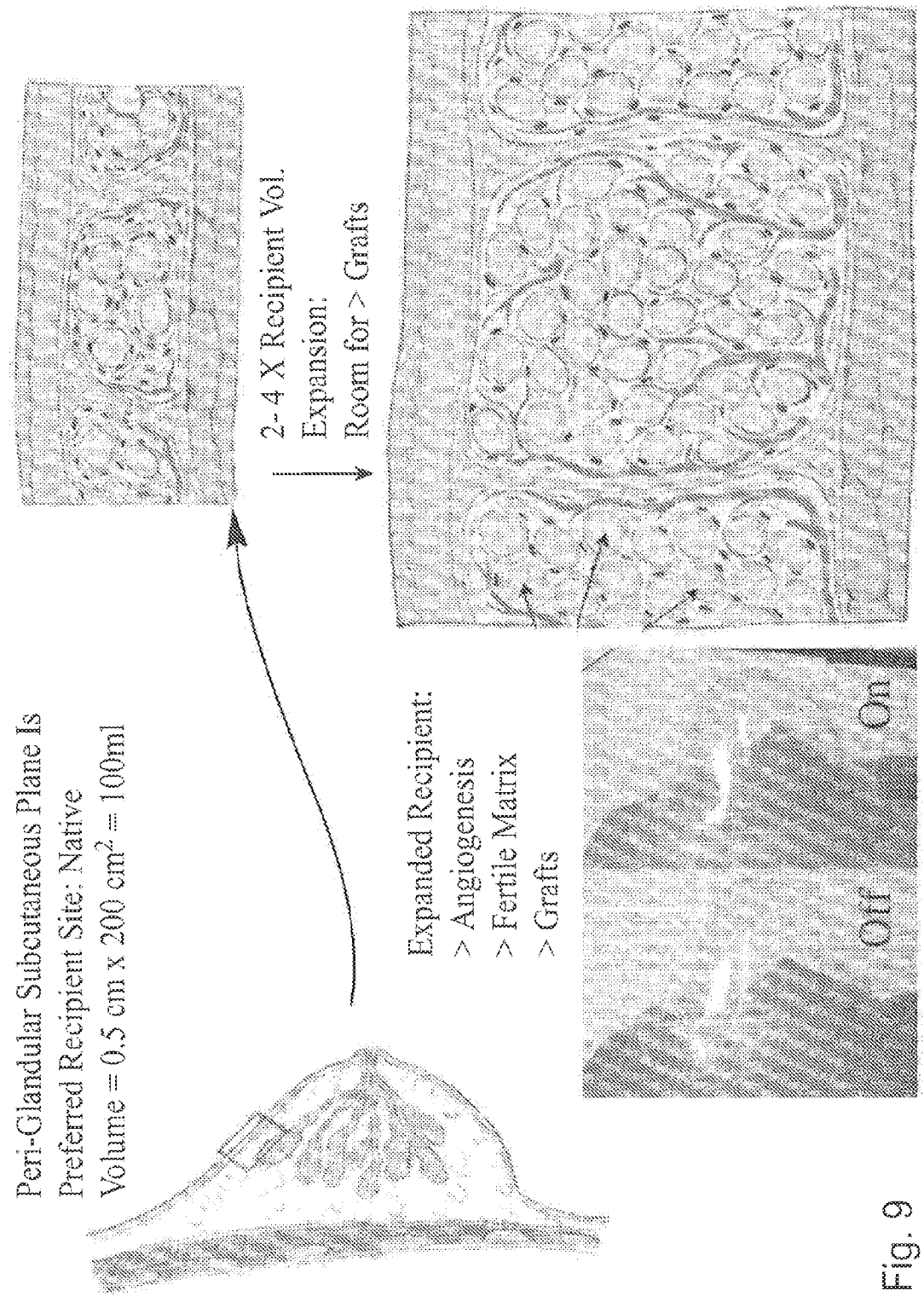
FIG. 9 shows the paradigm shift this invention has produced in the field of breast reconstruction in particular, and soft tissue regeneration in general.

Furthermore, this method might also offer an alternative to the reconstruction of the breast mound after lumpectomy, quadrantectomy, mastectomy, and radiation therapy. The current method of breast reconstruction consists of surgically inserting tissue expanders consisting of silicone bags and gradually inflating them with injectable saline over a period of weeks to expand and restore the skin envelope of the breast. The inflated expander creates a tissue void which needs to be replaced by an implant in a subsequent surgical procedure. In the proposed alternate application, external expansion can be used to generate the envelope and the recipient matrix space which will be gradually filled with liposuctioned fat grafts. The external expansion will also help generates the new blood vessels that can revascularize the grafts. The grafting may be done in one or multiple sessions over a period of weeks to months. This method will gradually transfer fat from other parts of the body and ensure the survival of that tissue to restore the breast mound (See FIG. 9).

In practicing this invention, the subject is advised to maintain their body weight. When the subject is of the female gender, the subject is further advised to take measures to avoid pregnancy during the procedure.

The degree of breast augmentation obtained by performing this procedure may be assessed by any number of methods. For example, breast augmentation volume may be derived from the 3D (3 dimensional) volumetric reconstruction of the MRI scans taken prior to and following the procedure or method. Typically, a baseline MRI to determine an initial pre-procedure volume is taken prior to initiating the first step of the method (i.e. before applying a distractive force to the un-injected breast). Additional MRI is performed at 3 months and 6 months post injection. A comparison of the breast volumes at 6 months relative to those at 3 months post injection permits an assessment of stability and long term graft survival result. Average augmentation volumes at 6 months post-procedure may be about 170 ml per breast and may range from about 90 ml to 220 ml. In some instances, the degree of breast augmentation attained may be limited by the amount of autologous fat that can be harvested from the subject.

In view of the limits to breast augmentation potentially imposed in certain instances by the amount of autologous fat that can be harvested from a subject, it is also contemplated that the fat sample can be obtained by methods other than direct removal and immediate reinjection into the subject. For example, the fat sample may be obtained by removing fat from the subject; propagating this removed fat outside of the subject, and collecting the fat sample that was expanded through propagation. Propagation in this context may be in an in vitro culture system specifically adapted to growth and expansion of fat. Alternatively, a sample of fat may be obtained by removing a living cell or living cells from the subject, propagating the cell or cells outside of the subject under conditions where the cell or cells will form a sample of fat; and collecting the sample of fat thus formed. In the context of a living cell or cell removed from the host, propagation of the cell or cells may be in an in vitro culture system that promotes the differentiation of a non-fat cell or fat cell progenitor cell into a fat cell. The non-fat cell may be a stem cell. One skilled in the art will recognize that a fat cell or fat cell progenitor may also be referred to as an adipose cell or adipose cell progenitor. Under these conditions the non-fat cell or fat cell progenitor cells may expand by cell division prior to becoming a fat cell. In the context of a living cell or cell removed from the host, propagation of the cell or cells may be in an in vitro culture system that promotes the expansion of a fully differentiated fat or adipose cell. In this case, expansion of the fully differentiated cell may occur by accumulation of fat within the cell rather than by cell division. Finally, it is contemplated that the living cell or cells removed horn the host under conditions where some combination of cell division and cell expansion results in the formation of a fat sample suitable for reinjection into the subject. Various methods and devices suitable for propagating cells outside of a source organism that may include a subject or another human are disclosed in U.S. Pat. No. 6,238,908, the contents of which are incorporated herein by reference in their entirety.

Also contemplated are methods whereby the engrafted stem cells are induced to regenerate lost tissue other than fat tissue in organs other than the breast.

Also contemplated are methods of obtaining the sample of fat from sources other than the subject. For example, the source of the sample of fat may be obtained from another human, a human that is genetically related to the subject, or a human that is a twin of the subject. Alternatively, the sample of fat may be obtained from a source that is as stem cell or cells derived from source other than the subject. The stem cell or cells may be propagated outside of the subject under conditions where said stem cell or cells form a sample of fat as described in the foregoing discussion of conditions used to obtain fat samples from a cell or cells derived from the subject.

It is further recognized that the entire procedure that comprises the steps of applying a distractive force to at least one breast of a subject, removing a sample of fat from the subject; injecting at least a portion of said sample of fat taken from the subject into said breast that was subjected to a vacuum, and then applying a distractive force to the breast injected with the subject's fat can be repeated on one or more breasts of a subject. Repeating the procedure may be desirable in instances where greater degrees of breast augmentation are sought.

While breast augmentation and reconstruction with liposuctioned fat is the example used here with a potential immediate clinical application, it would be understood by those of ordinary skill in the art that this invention pertains to three dimensional soft tissue grafting in general. The at least temporary pre-expansion of the recipient site by utilizing distractive forces improves the success and engraftment yield of the dispersed soft tissue cell grafts.

EXAMPLE

The following example of the invention is provided to illustrate the methods of this invention. Those skilled in the art will recognize that various modifications of the methods described herein may be made without departing from the gist of the invention.

Example One

Figure 3:
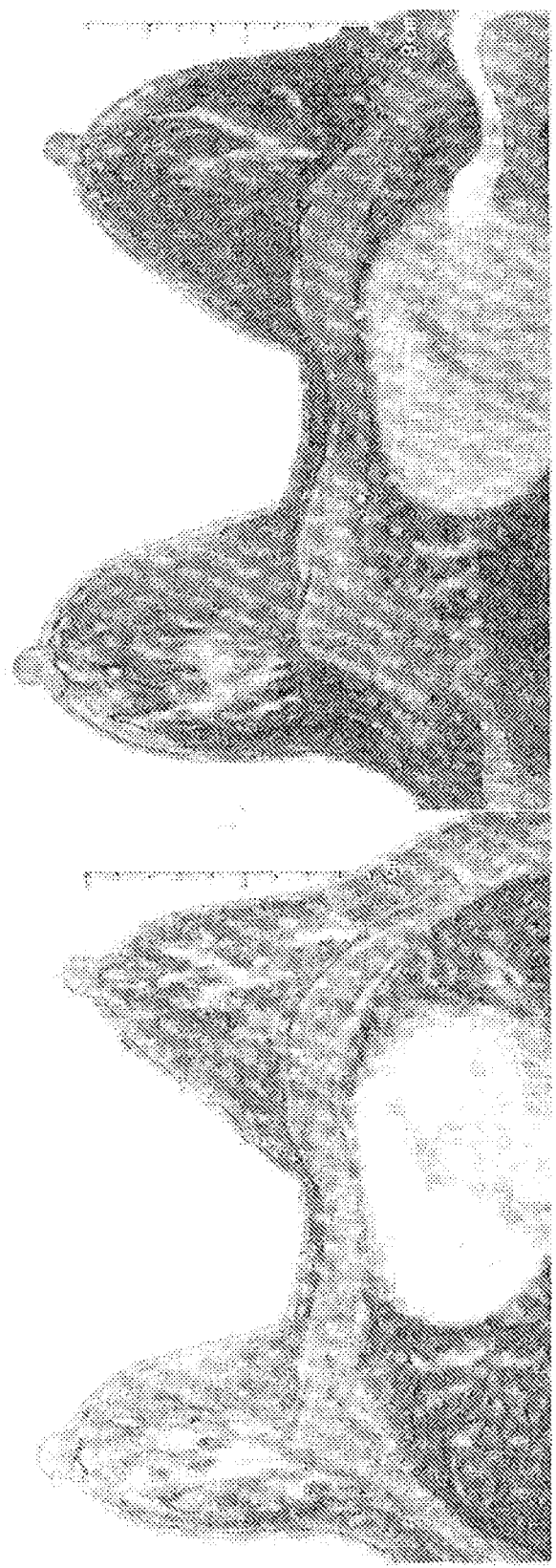
FIG. 3 illustrates magnetic resonance imaging results taken before and 3 months following the breast augmentation procedure.

After Institutional Review Board approval and informed consent of the subjects, 28 women underwent 30 fat grafting procedures on 55 breasts. This was achieved by performing one unilateral post cancer reconstruction with two grafting procedures, 24 bilateral primary breast augmentations with one grafting procedure and two bilateral primary breast augmentations with two grafting procedures. Following a baseline MRI (Magnetic Resonance Imaging) of the breast, an external breast tissue expander (Brava® Breast Enhancement and Shaping System, Brava, LLC; Coconut Grove, Fla.) was worn 10 hours per day for four weeks by the subjects. FIG. 1 shows a subject wearing an external breast tissue expander (Brava® Breast Enhancement and Shaping System, Brava, LLC; Coconut Grove, Fla.). For the 24 hour period immediately preceding the procedure, the subjects were asked to continuously use the external breast tissue expander and to come to the procedure still wearing the expander. This last pre-procedure step induces a marked temporary expansion of the subcutaneous plane creating more recipient space for the grafts. Under local tumescent anesthesia and sedation, using 12-14 G (gauge; 2-3 mm diameter) cannulas on 10-60 ml syringes, between 90 to 380 ml of fat per side was aspirated from the thighs, the flanks and the trochanters. The graft amount was limited by the ease of harvesting. The fat was separated from the serum and the tumescent fluid by decanting for a few minutes on a rack or by gently centrifuging it with a band operated centrifuge. It was then re-injected into the ipsilateral breast through a multitude of needle puncture sites in a three dimensional fanning pattern, micro-weaving the grafts using 3-10 ml syringes and a 12-140 (gauge; 2-3 mm diameter) cannulas. The three dimensional fanning pattern of injection is shown in FIG. 2. In 11 procedures some of the grafts were deliberately placed intraglandular. In the remaining procedures, the injection was limited to the subcutaneous plane and to the deep retroglandular space with strict avoidance of the breast parenchyma. Twelve hours post procedure, the subjects were asked to place the external breast tissue expander on and to keep wearing it as much as possible for the next few days to hold up the grafts as a stent daring the revascularization and early engraftment period. At three months post-procedure, a second MRI was obtained, and at 6 months post-procedure, a third MRI and a mammogram were obtained. Breast augmentation volume was derived from the 3D volumetric reconstruction of the MRI scans. FIG. 3 shows a comparison of the pre-procedure and 3 month post-procedure MRI scans of a subject.

Except for some temporary bruising and superficial skin blisters that healed uneventfully, there were no significant complications and all women returned to their normal activities within 3 to 4 days post-procedure. The patients were all pleased with the enlargement and improved appearance of their breasts and liposuctioned donor site. There were no palpable breast masses or nodules. The breast volume increase retained at 3 months remained constant at 6 months indicating permanent graft survival (3- vs. 6-month, $p>0.2$; paired t-test). The average augmentation volume at 6 months was 195 ml per breast and ranged from 100 ml to 320 ml. Graft survival averaged 90% and ranged from 120% (some of the women gained weight and in some cases the original grafted cells grew) to 70%. Though the numbers did not achieve statistical significance, graft survival was lower in the group where some of the grafts were injected intraglandular. More importantly, there was no fat necrosis in the group with strict periglandular grafting compared to the isolated intra-parenchymal foci of fat necrosis in the breasts that also received intraglandular grafts (0/14 vs. 5/11; $p=0.0087$, Fisher Exact test).

The inventor has some recent experimental animal (rat) data which demonstrates that the application of a distractive force over a period as short as two weeks is very angiogenic. By placing vacuum domes on the back of rats and applying vacuum over a period of two weeks, the inventor observed the formation of a very marked vascular and capillary network inside the domes that had vacuum applied. This observed intense neovascular response with the generation of a large new vascular network creates an ideal condition for successful graft take and survival. This angiogenic or neovascularization effect of pre-grafting expansion is one of the main advantages of this technique.

Figure 5:
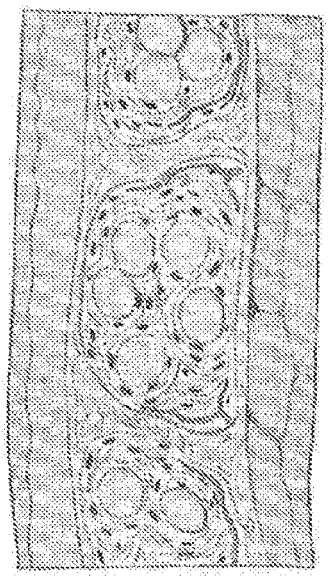
FIG. 5 illustrates an enlarged cross-sectional view of the subdermal periglandular plane taken from the indicated portion of FIG. 4.
Figure 6:
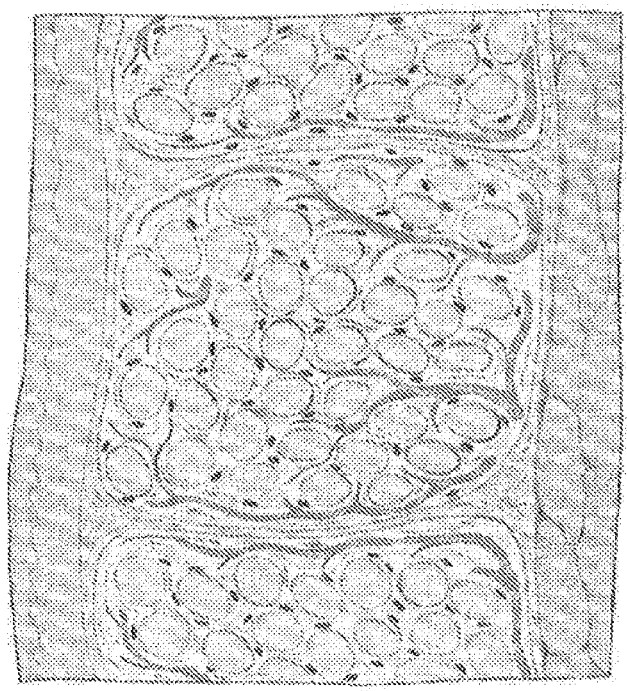
FIG. 6 illustrates the beneficial effect of preparation of the recipient tissue by the distractive force (external tissue expansion)
Figure 4:
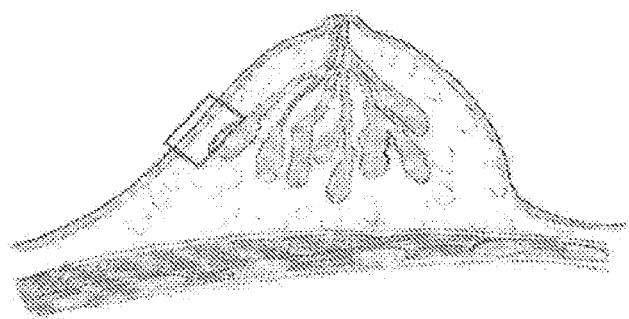
FIG. 4 illustrates a cross-sectional view of a woman's breast.
Figure 8:
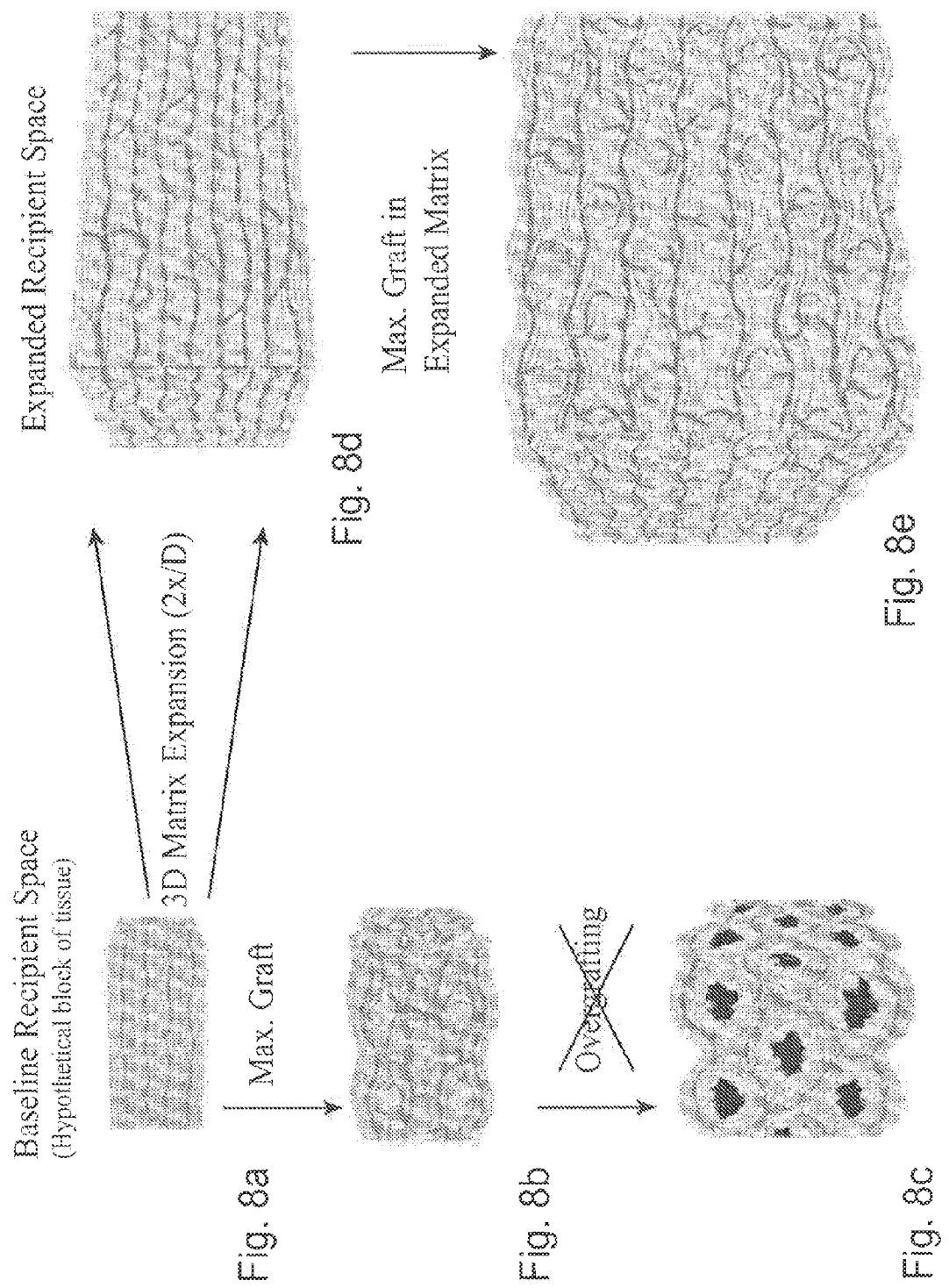
FIGS. 8a, 8b, 8c, 8d, and 8e illustrate a conceptual three dimensional block of soft tissue recipient, with FIG. 8a illustrating the state, FIG. 8b illustrating the maximum amount of most evenly dispersed micrograft grafts that can be successfully engrafted, FIG. 8c illustrating that attempts to stuff more grafts leads to necrosis because crowding interferes with revascularization of a significant portion of the graft, FIG. 8d illustrating the original block of soft tissue recipient after it has been subjected to expansive forces and increased in volume by doubling each of its dimensions and FIG. 8e illustrating how more grafts can now be successfully engrafted following expansion of the recipient block of soft tissue.

Yet another advantage of pre-grafting expansion is that it opens up the recipient space to allow more grafts placement with less crowding. It is important to avoid grafting in the breast parenchymal glandular tissue itself and the inventor has shown from his experimental work that the best recipient site is the subdermal periglandular plane. (In the cases where some grafts were deliberately placed in the glandular tissue a lower overall percentage graft take and more fat necrosis was found to occur). Pre expansion enlarges that preferred recipient plane to allow for more grafts there. It is well recognized by experts in the art of plastic surgery and grafting that improving the surface contact area interface between the graft and the recipient bed improves graft take and survival. The best graft survival is thought to occur when very small pieces (microdroplets) of fat are completely surrounded by a well vascularized recipient bed. These droplets should be separated from each other by recipient tissue and any crowding or graft to graft contact is thought to be detrimental. Hence the great beneficial effect of this pre-grafting expansion. The inventor generates the three dimensional network lattice and space to disperse more grafts with less crowding. The tissue may be likened to a sponge, and expansion enlarges that sponge allowing it to absorb many more "microdroplets" with better dispersion and less crowding. See FIGS. 4-6.

In summary, the inventor believes that he has with just his present work proven at least four major beneficial effects of pre-grafting expansion: 1—generation of new blood vessels or angiogenesis, which is well known to improve graft take, 2—generation of additional recipient space and three dimensional framework which makes room for more grafts to have better dispersion and less crowding, factors that optimize the crucial graft-to-recipient interface, 3—generation of an extracellular matrix fluid that is rich in growth factors and agents that render the space more fertile for graft success, and 4—a post operative stent like immobilization device that secures engraftment by allowing vascular ingrowth In view of the foregoing, it will be seen that the several advantages of the various aspects of the invention are achieved and attained.

The embodiments were chosen and described in order to best explain the principles of the invention and its practical application to thereby enable others skilled in the art to best utilize the invention in various embodiments and with various modifications as are suited to the particular use contemplated.

As various modifications could be made in the constructions and methods herein described and illustrated without departing from the scope of the invention, it is intended that all matter contained in the foregoing description or shown in the accompanying drawings shall be interpreted as illustrative rather than limiting. Thus, the breadth and scope of the present invention should not be limited by any of the above-described exemplary embodiments, but should be defined only in accordance with the following claims appended hereto and their equivalents.

What is claimed is:

1. A method for augmenting a region of soft tissue in a patient, the method comprising:
   a) applying a distractive force to the region of soft tissue sufficiently to expand the soft tissue; and
   b) injecting a material derived from fat into the region of soft tissue to enlarge the region of soft tissue;
   wherein the region of soft tissue is: a face; a scar; a buttock; a wrinkle line; a tissue atrophy related to disease, trauma or aging; or a breast of the patient.

2. The method of claim 1, wherein the distractive force is intermittently applied.

3. The method of claim 1, wherein the distractive force is continuously applied.

4. The method of claim 1, where in the distractive force is generated by vacuum pressure, an adhesive splint, a bandage, or a dome.

5. The method of claim 4, wherein the distractive force is generated by a vacuum pressure.

6. The method of claim 5, wherein the vacuum pressure is generated by positioning a vacuum device over the region of soft tissue and applying a vacuum.

7. The method of claim 6, wherein the vacuum device includes a pressure sensor.

8. The method of claim 6, wherein the vacuum device includes a servomechanism.

9. The method of claim 2, wherein the intermittent application of the distractive force to the region of soft tissue comprises cycling between a first vacuum pressure and a second vacuum pressure.

10. The method of claim 9, wherein the first vacuum pressure and the second vacuum pressure are the same.

11. The method of claim 9, wherein the first vacuum pressure and the second vacuum pressure are different.

12. The method of claim 9, wherein the first vacuum pressure is applied for a shorter time period than the second vacuum pressure.

13. The method of claim 9, wherein the second vacuum pressure is applied for a shorter period than the first vacuum pressure.

14. The method of claim 11, wherein the first vacuum pressure is higher than the second vacuum pressure.

15. The method of claim 11, wherein the second vacuum pressure is higher than the first vacuum pressure.

16. The method of claim 9, wherein the first vacuum pressure is a pressure between 15 mm Hg and 37 mm Hg, and the second vacuum pressure is a pressure between 15 mm Hg and 37 mm Hg.

17. The method of claim 16, wherein the first vacuum pressure is a pressure between 20 mm Hg and 25 mm Hg, and the second vacuum pressure is a pressure between 20 mm Hg and 25 mm Hg.

18. The method of claim 16, wherein the first vacuum pressure is a pressure between 35 mm Hg and 37 mm Hg and the second vacuum pressure is a pressure between 35 mm Hg and 37 mm Hg.

19. The method of claim 1, wherein the material derived from fat is obtained from the patient.

20. The method of claim 19, wherein the material derived from fat is obtained from an abdominal region, a thigh region, a flank region, a gluteal region, or a trochanter of the patient.

21. The method of claim 1, wherein the material derived from fat is obtained from a source other than the patient.

22. The method of claim 21, wherein the material derived from fat is obtained from an abdominal region, a thigh region, a flank region, a gluteal region, or a trochanter from the source other than the patient.

23. The method of claim 1, wherein the material derived from fat is a fat graft.

24. The method of claim 1, wherein the material derived from fat comprises fat or stem cells.

25. The method of claim 1, further comprising applying a distractive force to the enlarged region of soft tissue after injection of the fat graft.

26. The method of claim 25, wherein the distractive force is intermittently applied.

27. The method of claim 25, wherein the distractive force is continuously applied.

28. The method of claim 26, wherein the intermittent application of the distractive force to the region of soft tissue comprises cycling between a first vacuum pressure and a second vacuum pressure.

29. The method of claim 28, wherein the first vacuum pressure and the second vacuum pressure are the same.

30. The method of claim 28, wherein the first vacuum pressure and the second vacuum pressure are different.

31. The method of claim 28 wherein the first vacuum pressure is applied for a shorter time period than the second vacuum pressure.

32. The method of claim 28, wherein the second vacuum pressure is applied for a shorter period than the first vacuum pressure.

33. The method of claim 30, wherein the first vacuum pressure is higher than the second vacuum pressure.

34. The method of claim 30, wherein the second vacuum pressure is higher than the first vacuum pressure.

* * * * *